(12) United States Patent
Laing et al.

(10) Patent No.: US 7,746,454 B2
(45) Date of Patent: Jun. 29, 2010

(54) OPTICAL FIBER CONTINUOUS MEASUREMENT SYSTEM

(75) Inventors: Charles Frederick Laing, Wilmington, NC (US); Jody Paul Markley, Corning, NY (US); Randy C. Swingle, Athens, PA (US)

(73) Assignee: Corning Incorporated, Corning, NY (US)

( * ) Notice: Subject to any disclaimer, the term of this patent is extended or adjusted under 35 U.S.C. 154(b) by 114 days.

(21) Appl. No.: 12/079,440

(22) Filed: Mar. 27, 2008

(65) Prior Publication Data

US 2009/0244523 A1  Oct. 1, 2009

(51) Int. Cl.
    *G01N 21/00* (2006.01)
(52) U.S. Cl. .................................................. 356/73.1
(58) Field of Classification Search .................. None
    See application file for complete search history.

(56) References Cited

U.S. PATENT DOCUMENTS

| 4,838,690 | A | 6/1989 | Buckland et al. ............ 356/73.1 |
| 5,136,235 | A | * 8/1992 | Brandle et al. ................ 324/96 |
| 6,924,890 | B1 | 8/2005 | Vobian et al. ................. 356/73 |
| 6,947,637 | B2 | * 9/2005 | Smith ........................... 385/37 |

2003/0126892 A1  7/2003  Tsao et al. ...................... 65/485

FOREIGN PATENT DOCUMENTS

| DE | 29 11 410 | 9/1980 |
| EP | 0 421 657 | 4/1991 |
| GB | 1 557 155 | 12/1979 |
| JP | 56-128437 | 10/1981 |
| JP | 08-210948 | 8/1996 |

OTHER PUBLICATIONS

CEI/IEC 60793-1-47, "Measurement methods and test procedures—Macrobending loss", International Standard, Second edition, Sep. 2006, pp. 1-21.

* cited by examiner

*Primary Examiner*—Tu T Nguyen
(74) *Attorney, Agent, or Firm*—Matthew J. Mason (57) ABSTRACT

An optical fiber continuous measurement system continually measures at least one optical property along a length of optical fiber. The system includes a rotatable body onto which a reflector is secured. The reflector is optically coupled to an end of the optical fiber, thereby allowing light propagating from the optical fiber to the reflector to be reflected back along the length of the optical fiber toward a measuring device. The property to be measured is acquired as the fiber is wound from one rotatable body to the other. The system is particularly suited for measuring attenuation, including macrobend loss in which case a localized bending mechanism is employed, along the length of the fiber.

16 Claims, 5 Drawing Sheets

OPTICAL FIBER CONTINUOUS MEASUREMENT SYSTEM

BACKGROUND OF THE INVENTION

1. Field of the Invention

The present invention relates generally to continuous measurement of optical fiber, and particularly to continuous attenuation measurement of optical fiber, including continuous measurement of attenuation from bending ("macrobend loss").

2. Technical Background

Methods for measuring various properties of optical fiber often involve testing relatively short samples of stationary optical fiber. For example, methods for measuring light attenuation from bending ("macrobend loss") typically involve winding a short length of fiber a specified number of turns around a mandrel of a specific diameter or deploying the fiber through a series of guide grooves to hold the fiber at a specific bend radius. Bend sensitivity is determined by comparing spectral power of the fiber in the bend condition to spectral power through the fiber without a bend.

Such methods can be tedious and time consuming. Moreover, in the case of testing for resistance to macrobend loss, they can fail, as a practical matter, to simultaneously take into account multiple factors that can lead to an unacceptable level of macrobend loss. Such factors can include, for example, variations in manufacturing processes, variations as a result of optical fiber nonuniformity, variations in the manner in which optical fiber can be bent, and the unpredictability as to which sections of optical fiber may be ultimately bent in application. Such variations can lead to an unacceptable level of signal loss, even if only a very small percentage of an entire length of optical fiber is affected. Thus, it would be desirable to provide a method that can quickly and efficiently measure resistance to macrobend loss along an entire length of optical fiber.

SUMMARY OF THE INVENTION

One aspect of the invention includes a method of continuously measuring at least one optical property along a length of optical fiber. The method includes optically coupling a first end of an optical fiber to a reflector, wherein the reflector is secured to a first rotatable body. The method further includes optically coupling a second end of the optical fiber to a light source and a detector, wherein the light source is capable of passing light into the optical fiber and the detector is capable of detecting light passing out of the optical fiber. In addition, the method includes propagating at least a portion of the light from the light source through the optical fiber and to the reflector such that at least a portion of the light propagated from the optical fiber to the reflector is reflected back through the optical fiber and at least a portion of the light reflected back through the optical fiber is propagated to and detected by the detector. Finally, the method includes measuring the detected light for the at least one optical property as the first rotatable body is rotated.

In one preferred embodiment, the method also includes securing the second end of the optical fiber on a second rotatable body, wherein the second end of the optical fiber is optically coupled to the light source via a rotating optical coupler. In this embodiment, the second rotatable body is rotated while the first rotatable body is rotated such that the optical fiber is unwound from the second rotatable body as it is being wound on the first rotatable body.

In another preferred embodiment, the second rotatable body is held stationary and the fiber is paid out over the edge of the rotatable body. In this embodiment, because the rotatable body does not rotate, the optical coupling may be made directly to the second end of the optical fiber being tested. A guide mechanism may be employed to facilitate the fiber pay out over the edge of the rotatable body.

In a preferred embodiment the measured optical property is attenuation. In a particularly preferred embodiment, the measured optical property is attenuation due to macrobending or macrobend loss.

When the measured optical property is attenuation due to macrobending, the method can include translating a length of fiber to be measured through a localized bending mechanism while recording the additional optical attenuation caused by the localized bending in only that portion of the fiber that is within the bending mechanism. As the whole length of the fiber is passed through the bending mechanism, it is possible to make a continuous record of bend-induced optical attenuation, identifying regions of greater or lesser attenuation in the entire length of fiber.

A further aspect of the invention includes a device capable of performing the above-described method.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description serve to explain the principles and operations of the invention.

DETAILED DESCRIPTION OF TILE PREFERRED EMBODIMENTS

Reference will now be made in detail to the present preferred embodiments of the invention, examples of which are illustrated in the accompanying drawings. Whenever possible, the same reference numerals will be used throughout the drawings to refer to the same or like parts.

The present invention can provide for the continuous testing of optical fiber for at least one optical property. In a preferred embodiment, the present invention can provide for the continuous testing of attenuation, and in particular attenuation as a result of macrobend loss, along substantially longer lengths of optical fiber than were typically tested under previous test methods wherein the optical fiber was stationary during the test. For example, whereas previous test methods for macrobend loss typically involved testing optical fiber lengths of less than 1 meter, embodiments of the present invention can provide for the testing of optical fiber having a length of at least 1 meter, such as at least 10 meters, and further such as at least 100 meters, including at least 1 kilometer, and further including at least 10 kilometers, and even further including at least 100 kilometers.

In addition, the present invention can provide for continuous and repeated measurement of at least one optical property as optical fiber is moved along at least a portion of a testing apparatus or system. In a preferred embodiment, optical fiber is moved along or through a testing apparatus at a rate of at least 0.1 meters per second, such as at least 0.5 meter per second, further such as at least 1 meter per second, and further such as at least 5 meters per second, and even further such as at least 10 meters per second.

In the case of testing for macrobend loss, a portion of a testing apparatus can include a bending mechanism that includes one or more pulleys, wherein the fiber being tested is turned around at least a portion of each pulley. In preferred embodiments, the fiber being tested may be turned in any amount up to 360° around each pulley and may be turned in different amounts around different pulleys. For example, the fiber being tested may make a quarter turn (i.e., 90° turn), a half turn (i.e., 180° turn), a three quarter turn (i.e., 270° turn) or a full turn (i.e., 360° turn) around each pulley (or any turn amount in between). In further preferred embodiments, the fiber being tested may be turned more than once around the same pulley (i.e., greater than 360°). For example, the fiber being tested may be turned one and a half times around the same pulley or may be turned two or more times around the same pulley.

In a preferred embodiment, the testing apparatus can include a bending mechanism that includes at least two pulleys and in a further preferred embodiment, the testing apparatus can include at least four pulleys. At least one pulley may be at an angle relative to at least one other pulley. For example, in a preferred embodiment, the axis of at least one pulley may be perpendicular (i.e., at a 90° angle) relative to the axis of at least one other pulley. In a further preferred embodiment, the axis of at least one pulley may be at another angle, such as a 45° angle, relative to the axis of at least one other pulley.

While pulley diameters are not to be understood as being limited to any specific value, in a preferred embodiment at least one pulley diameter is less than or equal to 60 millimeters, such as less than or equal to 30 millimeters, and further such as less than or equal to 15 millimeters. For example, at least one pulley diameter can be from 10 to 30 millimeters, including from 10 to 20 millimeters. In a preferred embodiment, when two or more pulleys are used (including, but not limited to where at least one pulley is perpendicular to at least one other pulley), each pulley can have a diameter that is less than or equal to 30 millimeters, such as less than or equal to 15 millimeters. For example, each pulley diameter can be from 10 to 30 millimeters, including from 10 to 20 millimeters.

In a preferred embodiment, when two or more pulleys are used, the pulleys can be in relatively close proximity to each other such that a relatively short portion of the fiber being tested is in the pulley system at any given time (the length of the fiber in the pulley system being the length of fiber between the point where the fiber enters the first pulley and the point where it exits the last pulley). For example, in a preferred embodiment, up to 500 millimeters of the fiber may be in the pulley system at any given time, such as from 50 millimeters to 350 millimeters, and further such as from 100 millimeters to 250 millimeters.

The testing apparatus can include a measurement device that, in preferred embodiments, is capable of measuring at least one optical property at regular time intervals. For example, in a preferred embodiment, the measurement device is capable of measuring at least one optical property at least 1 time per second, including at least 10 times per second, further including at least 100 times per second, and even further including at least 1,000 times per second. In a preferred embodiment, the at least one optical property is macrobend loss.

Accordingly, depending on the rate at which optical fiber is moved along or through a testing device and the rate at which the measuring device measures at least one optical property, measurements for at least one optical property can be taken each time a given length of fiber has moved along or through the device. For example, if optical fiber is moving through a testing device at a rate of 1 meter per second and the measuring device is measuring at least one optical property 100 times per second, then the at least one optical property is being measured each time $1/100^{th}$ of a meter (or 1 centimeter) of optical fiber is moved through the device. In preferred embodiments, the at least one optical property is being measured each time up to 1 meter of optical fiber is moved through the device, such as each time up to 10 centimeters of optical fiber is moved through the device, and further such as each time up to 1 centimeter of optical fiber is moved through the device, and even further such as each time up to 1 millimeter of optical fiber is moved through the device. In particularly preferred embodiments, at least one optical property is measured each time 1 millimeter to 1 centimeter of optical fiber is moved through the device, such as each time 2 millimeters to 6 millimeters of optical fiber is moved through the device, including each time 3 millimeters to 5 millimeters of optical fiber is moved through the device.

Embodiments of the present invention can provide for the measurement of at least one optical property along the entire length of the optical fiber. For example, resistance to macrobend loss can be measured at least once when each discrete point along the entire length of the fiber is in a pulley or pulley system. For example, if 200 millimeters of fiber is in a pulley system at any given time, the fiber is moving through the testing device at a rate of 2 meters per second, and the measuring device is taking measurements at a rate of 100 times per second, then each discrete point along the fiber length is in the pulley system for 0.1 second during which time the measuring device has taken 10 measurements. In preferred embodiments, the measuring device will take from 1 to 100 measurements each time a discrete point along the entire length of the fiber is in a pulley or pulley system, such as from 10 to 25 measurements each time a discrete point along the entire length of the fiber is in a pulley or pulley system.

In preferred embodiments, the optical fiber under test is initially wound on a first rotatable body, wherein the first rotatable body is a spool (i.e., a "payout spool"). The optical fiber under test can then be moved along or through a testing apparatus or system by first threading an outside or front end of the fiber through the apparatus or system and securing it to a second rotatable body, wherein the second rotatable body is also a spool (i.e., a "take-up spool"). Then, a desired amount of fiber can be unwound from the first rotatable body, moved along or through the testing apparatus or system, and wound on the second rotatable body by rotating at least the second rotatable body (to which the outside or front end of the fiber has been secured). As the optical fiber is moved along or through the testing apparatus or system, at least one optical property can be repeatedly measured and recorded.

In preferred embodiments, the movement of optical fiber along or through a testing apparatus or system can be stopped if at least one optical property is measured as being above or below a predetermined value or range. For example, if the at least one optical property is macrobend loss, the movement of optical fiber through a testing apparatus can be stopped if macrobend loss is measured as being above a predetermined value. This can allow the user to pinpoint sections of optical fiber that fail to meet predetermined specifications for resistance to macrobend loss by observing the length of fiber in a pulley or pulley system at the time the apparatus was stopped. This length (or a portion thereof) can be optionally removed and examined.

In preferred embodiments, when the at least one optical property is macrobend loss, the position along the optical fiber of the length of the optical fiber that is being passed around a portion of at least one pulley can be recorded each time macrobend loss is measured. This can allow the user to pinpoint sections of optical fiber that fail to meet predetermined specifications for resistance to macrobend loss during or after an entire length optical fiber has been passed through a testing apparatus or system. These sections (or portions thereof) can be optionally removed and examined.

Figure 1:
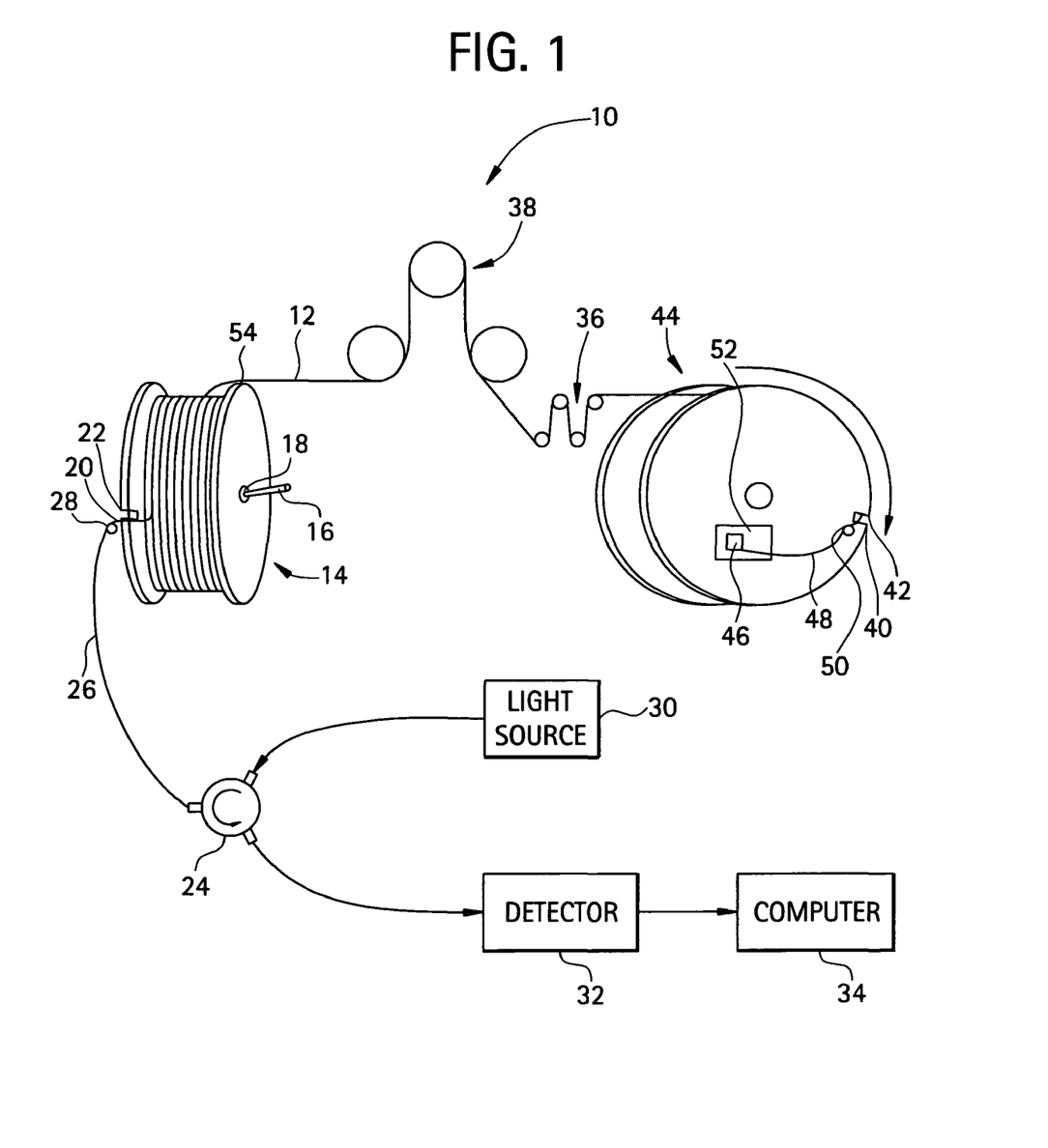
FIG. 1 is a schematic representation of a first embodiment of the present invention having a stationary payout spool.

Referring now to FIG. 1, a first embodiment of the invention is illustrated wherein a screening device 10 that is typically used for mechanical strength testing of optical fiber has been modified for continuous macrobend loss testing of optical fiber. In the embodiment illustrated, optical fiber under test 12 is wound on a payout spool 14 that is mounted onto a fixture 16 located on the payout side of the device 10. The fixture 16 holds the payout spool 14 so that its hub 18 is parallel to the path of the fiber under test 12 through the device. The inside or back end 20 of the fiber under test 12 is passed through a slot 22 in payout spool 14 and optically coupled to an optical circulator 24 by a short pigtail fiber 26 that is fusion spliced at splice joint 28 to the fiber under test 12. Optical circulator 24 is optically coupled to a light source 30 through the pass-through port of the circulator, thereby allowing light to propagate from the light source 30 to the fiber under test 12 via optical circulator 24 and pigtail fiber 26 (i.e., "forward propagation"). Optical circulator 24 is also optically coupled to a detector 32 through the backward-propagation port of the circulator, thereby allowing light to propagate from the fiber under test 12 to the detector 32 via the pigtail fiber 26 and optical circulator 24 (i.e., "backward propagation").

In a preferred embodiment, light source 30 is an amplified spontaneous emission (ASE) source operating at the specification wavelength (preferably 1550 nm). Other light sources may also be used, including lasers or filtered broadband incandescent lamps. In preferred embodiments, polarized light should generally be avoided to eliminate polarization-dependent loss effects.

In a preferred embodiment, a computer or digital data acquisition system 34 collects and processes the data from detector 32. In a preferred embodiment, detector 32 is a power meter.

Device 10 includes a bending mechanism pulley system 36 (shown in the illustrated embodiment as four pulleys) around which the fiber under test 12 can be wound in order to provide a high bending environment for macrobend loss testing. Device 10 further includes one or more additional pulleys 38 inherent to a screening device that allow for the proper tensioning and guidance of the fiber under test 12 through the device. Such pulleys 38 will typically have a substantially larger diameter than the pulleys within pulley system 36 such that any macrobend loss induced by winding the fiber under test 12 around pulleys 38 will be negligible when compared to the macrobend loss induced as a result of winding the fiber under test 12 around pulleys within pulley system 36. Pulleys within pulley system 36 can be arranged such that the axis of at least one pulley within pulley system 36 can be perpendicular to the axis of at least one other pulley within pulley system 36 (not shown).

In the embodiment illustrated, the fiber under test 12 is threaded through device 10, including pulley system 36 and additional pulleys 38, and the outside or first end 40 of the fiber under test 12 is secured to a slot 42 in a take-up spool 44. Front end 40 of the fiber under test 12 is optically coupled to a reflector 46 by a short pigtail fiber 48 that is fusion spliced at splice joint 50 to the fiber under test 12 (a mechanical splice could also be used, provided it is stable). Reflector 46 and short pigtail fiber 48 are secured to a take-up arbor bolster plate 52 that is secured to take-up spool 44 such that when take-up spool 44 is rotated, front end 40 of the fiber under test 12, pigtail fiber 48, and reflector 46 all rotate with take-up spool 44.

In the embodiment illustrated, once the fiber under test 12 is secured to take-up spool 44 and optically coupled to reflector 46, light from light source 30 is propagated along the length of the fiber to reflector 46 and then reflected back along the length of the fiber to detector 32. Take-up spool 44 is then rotated so that the fiber under test 12 is continually unwound from payout spool 14, passed through device 10, and wound on take-up spool 44. This allows each point along the length of the fiber under test 12 to pass through pulley system 36 during which time light reflected back to detector 32 can be measured continually or at regular intervals. During this time, the payout spool 14 in the embodiment shown in FIG. 1 is not rotating. Instead, the fiber under test 12 is being continually unwound from the payout spool 14 by being passed over a flange 54 of the spool. In a preferred embodiment, fixture 16 includes a guide arm (not shown) that rotates about payout spool axis and guides the fiber being paid out over flange 54.

Figure 2:
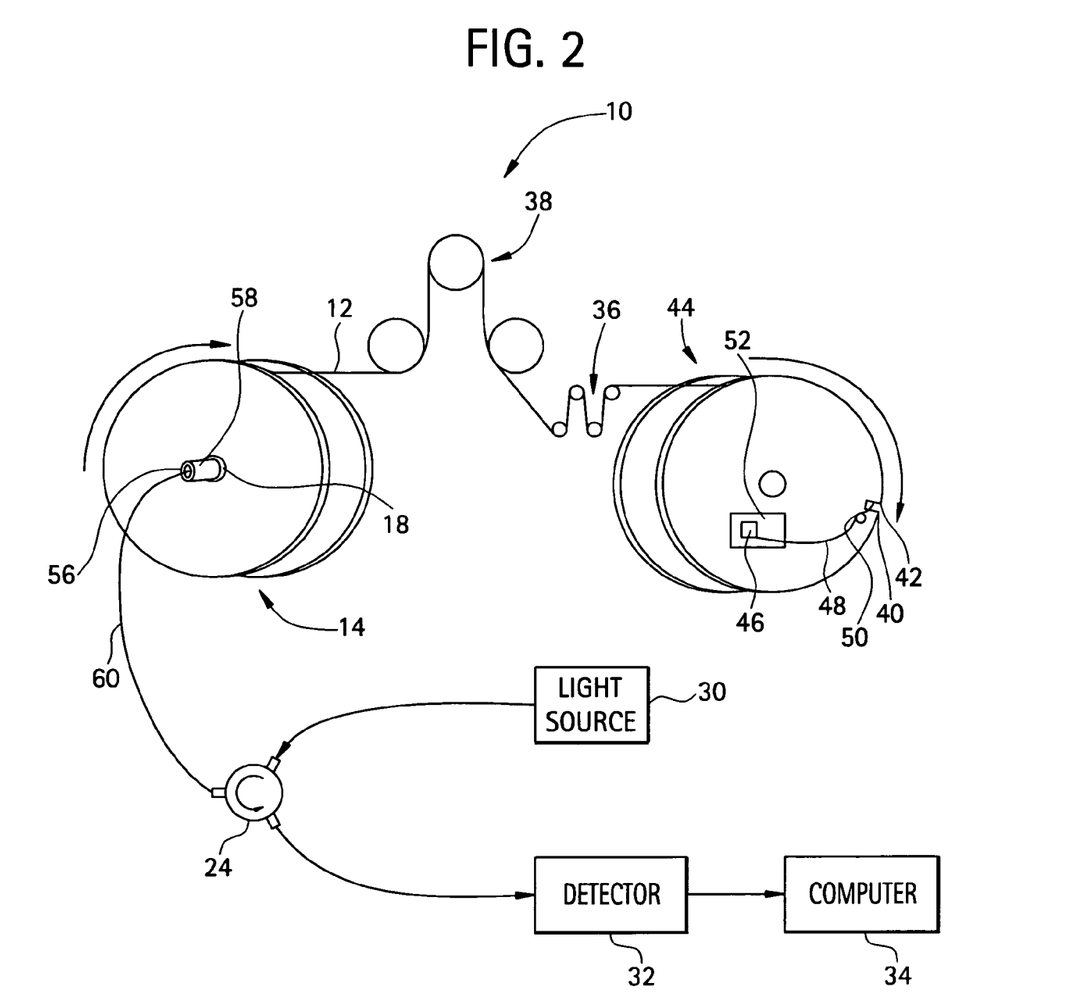
FIG. 2 is a schematic representation of a second embodiment of the present invention having a rotating payout spool.

Referring now to FIG. 2, an alternative embodiment of the present invention is shown. In FIG. 2, payout spool 14 is mounted on a payout arbor shaft 56 such that its axis of rotation 18 is perpendicular to the path of the fiber under test 12 through the device. The payout arbor shaft 56 is modified to accept a rotating optical coupler 58 through the center of the shaft (other embodiments could include other methods of optical coupling to moving fiber, such as injection devices (LIDs) or more than one rotating optical coupling). The inside or back end of the fiber under test is deployed through a slot on the inside of the payout spool and fusion spliced to a short pigtail fiber (not shown). The pigtail is optically coupled to the inside lead of the rotating optical coupler 58 (the payout arbor is further modified via a machined slot, allowing coupling to the pigtail fiber) with a bulkhead connector on the rear surface of the payout spool. The rotating optical coupler 58 is optically coupled to an optical circulator 24 by a short outside pigtail fiber 60.

In the embodiment shown in FIG. 2, payout spool 14 is capable of rotating at the same time that take-up spool 44 is rotating (at the same or substantially the same speed) such that when both spools are rotating, the fiber under test 12 is continually unwound from payout spool 14, passed through device 10, and wound on take-up spool 44. The use of rotating optical coupler 58 in this embodiment allows light from light source 30 to be propagated to the fiber under test and further allows light from the fiber under test (i.e., light reflected back by reflector 46) to be propagated to detector 32 as payout spool 14 is rotating.

In either the embodiment shown in FIG. 1 or the embodiment shown in FIG. 2, the computer or digital data acquisition system 34 can generate a signal that stops take-up spool 44 and/or payout spool 14 from rotating if a reading or measurement of macrobend loss is taken that is higher than a predetermined value. The computer or digital data acquisition system 34 can also record the position along the length of the fiber under test 12 that is being passed through pulley system 36 at any given time. This can allow the user to pinpoint the portion of the fiber under test 12 that is in the pulley system 36 at the time a reading or measurement of macrobend loss is above a predetermined value.

Attenuation of light in an optical fiber in the above-described embodiments typically includes a fixed loss due to fiber attenuation, a coupling loss, and reflector loss, plus a varying term due to the macrobend sensitivity of the portion of the fiber in the bending mechanism at any given point within the length of the fiber as it passes through the bending mechanism while being translated from the second rotatable body to the first rotatable body. Therefore, in order to determine the portion of total attenuation resulting from macrobend loss, the embodiments shown in FIGS. 1 and 2 can be used in a two-step process for measuring attenuation wherein in a first step, non-macrobend attenuation is measured by threading the fiber under test 12 through device 10 without winding or threading the fiber through pulley system 36 and then measuring the light reflected back to detector 32 continually or at regular intervals as the fiber under test is wound on take-up spool 44 and unwound from payout spool 14. This allows the user to determine the average amount of attenuation attributable to baseline system conditions. Then, in a second step, the fiber under test 12 can be wound through pulley system 36 and attenuation measurements taken as described above, wherein each part of the fiber under test 12 passes through pulley system 36 and light reflected back to detector 32 is measured continually or at regular intervals as the fiber under test is wound on take-up spool 44 and unwound from payout spool 14. This allows the user to determine the amount of attenuation attributable to macrobend loss at a given point along the length of the fiber by subtracting the averaged baseline attenuation measured in the first step from the attenuation measured in the second step.

Figure 3:
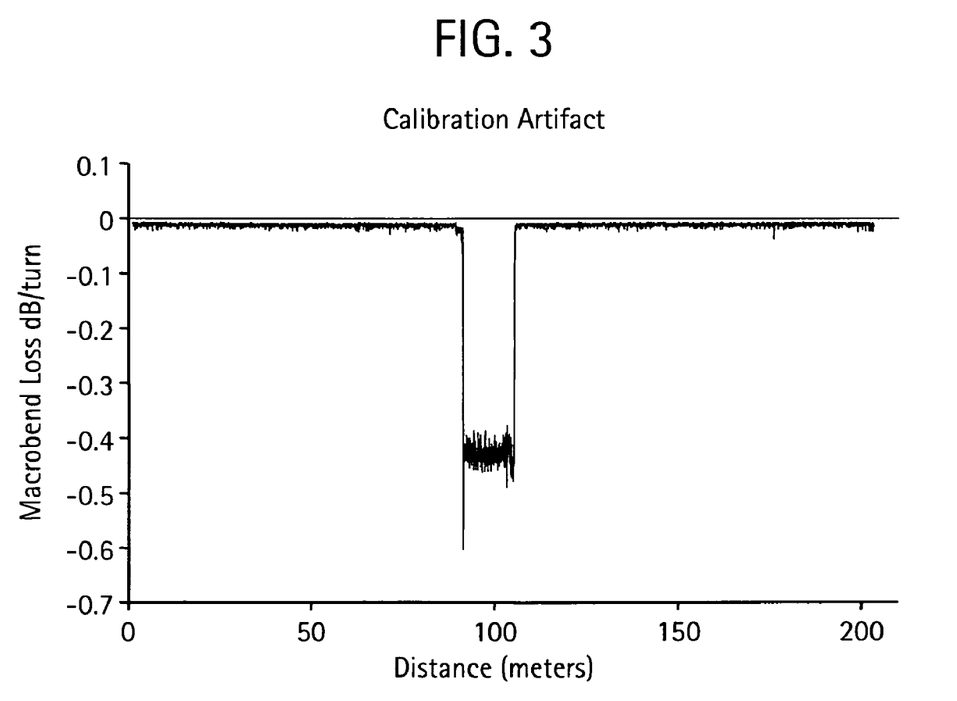
FIG. 3 is a plot showing values of macrobend loss of a calibration artifact having a portion of fiber with known higher macrobend loss characteristics spliced within a fiber with known lower macrobend loss characteristics.

Measurements taken in either of the embodiments shown in FIGS. 1 or 2 can be calibrated by producing an artifact with regions of known macrobend loss as measured by the sampling macrobend loss measurement method described in IEC 60793-1-47. Such an artifact can be produced by fusion splicing a section known to have worse macrobend loss attributes into a longer section known to have better macrobend loss attributes. The artifact can then be wound through pulley system 36 and attenuation measurements taken as described above, wherein each part of the artifact passes through pulley system 36 and light reflected back to detector 32 is measured continually or at regular intervals as the artifact is wound on take-up spool 44 and unwound from payout spool 14. FIG. 3 shows the results of using this technique to measure macrobending loss along the length of a calibration artifact that was produced by a splicing a portion of fiber with a known macrobend loss of 0.45 dB/turn (around a 10 mm diameter pulley at a wavelength of 1550 nm) within a fiber with a known macrobend loss of 0.012 dB/turn (around a 10 mm diameter pulley at a wavelength of 1550 nm).

EXAMPLES

The invention will be further clarified by the following examples.

Figure 4:
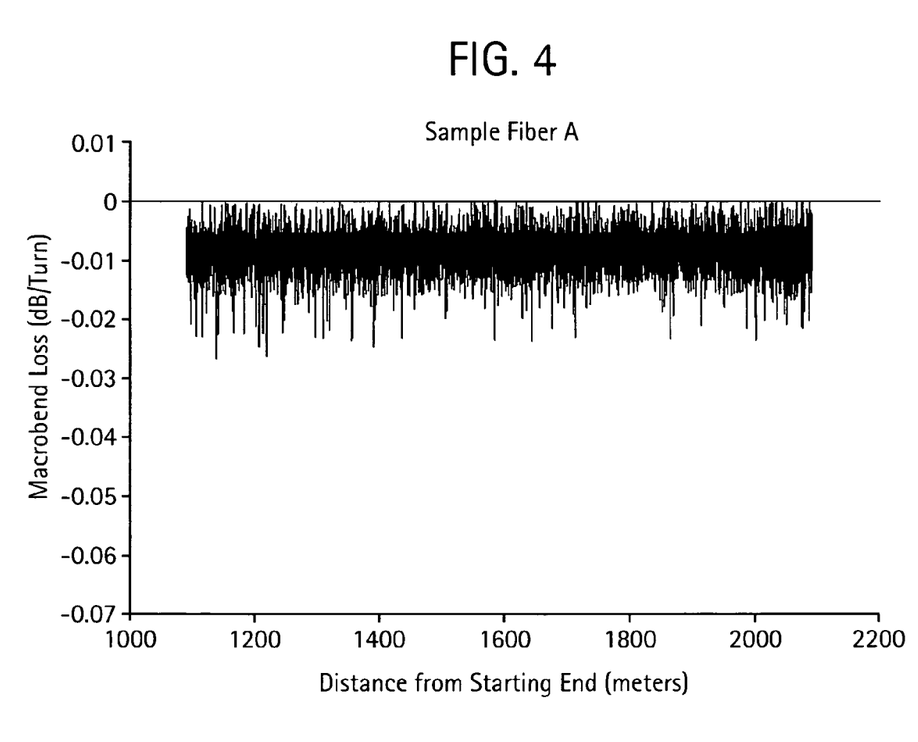
FIG. 4 is a plot showing values of macrobend loss along the length of an optical fiber as measured by an embodiment of the present invention.
Figure 5:
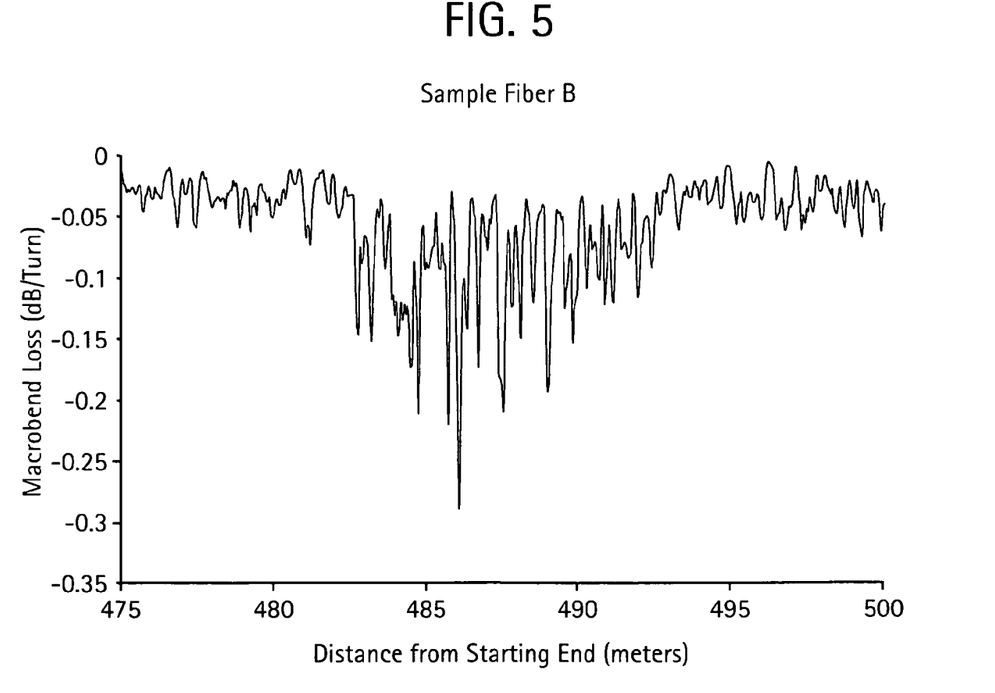
FIG. 5 is a plot showing values of macrobend loss along the length of another optical fiber as measured by an embodiment of the present invention.

An Agilent amplified spontaneous emission source at 1550 nm was optically coupled to an optical fiber in accordance with the embodiment described above with reference to FIG. 1, wherein the fiber was scanned (i.e., moved through the testing apparatus) at a rate of 0.5 meters per second. Reflected power was measured with a Newport 2832-C power meter and 818-IS-1 detector at a rate of 500 samples per second with a running average of 50 samples being stored. FIG. 4 shows results of testing a first optical fiber length ("Sample Fiber A") with this technique. FIG. 5 shows results of testing a second optical fiber length ("Sample Fiber B") with this technique. As can be seen from comparing FIGS. 4 and 5, Sample Fiber B is shown as having relatively worse macrobend loss uniformity characteristics than Sample Fiber A.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

What is claimed is:

1. A method of continuously measuring at least one optical property along a length of optical fiber, the method comprising:

optically coupling a first end of an optical fiber to a reflector, wherein the reflector is secured to a first rotatable body and a second end of the optical fiber is secured to a second rotatable body;

optically coupling the second end of the optical fiber to a light source and a detector, wherein the second end of the optical fiber is optically coupled to the light source via a rotating optical coupler and wherein the light source is capable of passing light into the optical fiber and the detector is capable of detecting light passing out of the optical fiber;

propagating at least a portion of the light from the light source through the optical fiber and to the reflector such that at least a portion of the light propagated from the optical fiber to the reflector is reflected back through the optical fiber and at least a portion of the light reflected back through the optical fiber is propagated to and detected by the detector; and measuring the detected light for the at least one optical property as the first rotatable body is rotated and the second rotatable body is rotated such that the optical fiber is unwound from the second rotatable body as it is being wound on the first rotatable body.

2. The method of claim 1, wherein the at least one optical property is macrobend loss and the method comprises passing the fiber around at least a portion of at least one pulley.

3. The method of claim 2, wherein the at least one pulley has a diameter less than or equal to 60 millimeters.

4. The method of claim 2, wherein the method comprises passing the fiber around at least a portion of at least two pulleys, wherein the axis of at least one of said pulleys is perpendicular to the axis of at least one other of said pulleys.

5. The method of claim 4, wherein each pulley has a diameter of less than or equal to 60 millimeters.

6. The method of claim 2, wherein the first rotatable body stops rotating and the second rotatable body stops rotating if macrobend loss is measured as being above a predetermined value.

7. The method of claim 2, wherein the position along the optical fiber of the portion of the optical fiber that is being passed around a portion of at least one pulley is recorded each time macrobend loss is measured.

8. The method of claim 2, wherein macrobend loss is measured at least 10 times per second.

9. The method of claim 2, wherein macrobend loss is measured at least 100 times per second.

10. The method of claim 1, wherein the optical fiber is wound on the first rotatable body at a rate of at least 0.1 meter per second.

11. The method of claim 1, wherein the optical fiber has a length of at least 10 meters.

12. The method of claim 1, wherein the optical fiber has a length of at least 100 meters.

13. The method of claim 1, wherein the at least one optical property is measured at least 10 times per second.

14. The method of claim 1, wherein the at least one optical property is measured at least 100 times per second.

15. The method of claim 1, wherein the first rotatable body stops rotating and the second rotatable body stops rotating if the at least one optical property is measured as being above or below a predetermined value or range.

16. A device capable of performing the method of claim 1.

* * * * *